(12) United States Patent
Yamashiro et al.

(10) Patent No.: US 8,993,000 B2
(45) Date of Patent: Mar. 31, 2015

(54) METHOD FOR INDUCING DIFFERENTIATION OF DENTAL PULP CELLS INTO ODONTOBLASTS

(75) Inventors: Takashi Yamashiro, Okayama (JP); Hiroshi Kurosaka, Okayama (JP); Noriaki Kawanabe, Okayama (JP)

(73) Assignee: National University Corporation Okayama University, Okayama-shi, Okayama (JP)

( * ) Notice: Subject to any disclaimer, the term of this patent is extended or adjusted under 35 U.S.C. 154(b) by 307 days.

(21) Appl. No.: 13/510,535

(22) PCT Filed: Nov. 16, 2010

(86) PCT No.: PCT/JP2010/070330
§ 371 (c)(1),
(2), (4) Date: May 25, 2012

(87) PCT Pub. No.: WO2011/062147
PCT Pub. Date: May 26, 2011

(65) Prior Publication Data
US 2012/0231091 A1 Sep. 13, 2012

(30) Foreign Application Priority Data
Nov. 17, 2009 (JP) .................................. 2009-262378

(51) Int. Cl.
| | | |
|---|---|---|
| *C12N 5/0775* | (2010.01) | |
| *A61K 31/00* | (2006.01) | |
| *A61K 33/14* | (2006.01) | |
| *A61K 33/40* | (2006.01) | |
| *A61K 36/258* | (2006.01) | |
| *A61K 38/17* | (2006.01) | |
| *C12N 5/077* | (2010.01) | |
| *A61K 38/00* | (2006.01) | |

(52) U.S. Cl.
CPC ......... *A61K 31/00* (2013.01); *C12N 2502/1311* (2013.01); *C12N 2501/00* (2013.01); *C12N 5/0664* (2013.01); *C12N 2506/21* (2013.01); *A61K 33/14* (2013.01); *A61K 33/40* (2013.01); *A61K 36/258* (2013.01); *A61K 38/1709* (2013.01); *C12N 5/0654* (2013.01); *C12N 2500/05* (2013.01); *C12N 2501/415* (2013.01)
USPC ........................................................ 424/662

(58) Field of Classification Search
CPC .............................................. C12N 2501/415
See application file for complete search history.

(56) References Cited

U.S. PATENT DOCUMENTS

| | | | | |
|---|---|---|---|---|
| 8,541,177 B2* | 9/2013 | Chan | ............... | 435/7.1 |
| 2006/0147435 A1* | 7/2006 | Moon et al. | ................ | 424/93.21 |
| 2009/0035282 A1* | 2/2009 | Schierholz et al. | .......... | 424/93.7 |
| 2011/0008287 A1* | 1/2011 | Van Der Burg et al. | ...... | 424/85.4 |
| 2012/0245086 A1* | 9/2012 | Chung et al. | .................... | 514/6.9 |
| 2013/0095116 A1* | 4/2013 | Gurney et al. | ............. | 424/172.1 |
| 2014/0093481 A1* | 4/2014 | Mao et al. | .................... | 424/93.7 |

FOREIGN PATENT DOCUMENTS

| | | |
|---|---|---|
| JP | 06-340555 A | 12/1994 |
| JP | 2009-249344 A | 10/2009 |
| WO | WO 2008/120720 A | 10/2008 |

OTHER PUBLICATIONS

Han et al. (2014) ("Wnt signaling inhibits the odontoblast-like differentiation of Dental Pulp Cells through Activation of Runx2", PLOS One, vol. 9, issue 2, pp. 1-10.*
Wnag et al. (2009) Apc inhibition of Wnt signaling regulates supernumerary tooth formation during embryogenesis and throughout adulthood, Dev. Disease, vol. 136, pp. 1939-1849.*
Papagerakis et al. (1999) Evidence for Regulation of Amelogenin Gene Expression by 1,25-Dihydroxyvitamin D3 In Vivo, J. Cell. Biochem., vol. 76, pp. 194-205.*
Wang et al. (2004) QSulf1, a heparan sulfate 6-O-endosulfatase, inhibits fibroblast growth factor signaling in mesoderm induction and angiogenesis, Proc. Natl. Sci. Acad., vol. 101, pp. 4833-4838.*
Hayano et al. (2012) Roles of Heparan Sulfate Sulfation in Dentinogenesis, J. Biol. Chem., vol. 287, No. 15, pp. 12217-12229.*
Nakashima et al. (2005) The Application of Tissue Engineering to Regeneration of Pulp and Dentin in Endodontics, J. Endodontics, vol. 31, pp. 711-718.*
Cantorna et al. (2004) Vitamin D status, 1,25-dihydroxyvitamin D3, and the immune system Am J Clin Nutr, vol. 80(suppl), vol. 17, pp. 17S-20S.*
R. N. D'Souza et al: "Gene Expression Patterns of Murine Dentin Matrix Protein 1 (Dmp1) and Dentin Sialophosphoprotein (DSPP) Suggest Distinct Developmental Functions In Vivo", Journal of Bone and Mineral Research, vol. 12, No. 12, Dec. 1, 1997, pp. 2040-2049.
Shangxi Xiao et al: Nature Genetics, val. 27, No. 2, Feb. 1, 2001, pp. 201-204.
X. Ai et al: "QSulf1 remodels the 6-0 sulfation states of cell surface heparan sulfate proteoglycans to promote Wnt signaling", The Journal of Cell Biology, vol. 162, No. 2, Jul. 1, 2003, pp. 341-351.
Shortkroff et al: "Alteration of matrix glycosaminoglycans diminishes articular chondrocytes' response to a canonical Wnt signal", Osteoarthritis and Cartilage, vol. 15, No. 2, Jan. 26, 2007, pp. 14 7-1 54.
Wang, C. et al.: "Effect of Wnt6 on human dental papilla cells in vitro.", J. Endod., vol. 36, No. 2, Oct. 23, 2009, pp. 238-243.

(Continued)

*Primary Examiner* — Maryam Monshipouri
*Assistant Examiner* — Samuel Liu
(74) *Attorney, Agent, or Firm* — Don D. Cha; Hamilton DeSanctis & Cha, LLP

(57) ABSTRACT

Provided is an efficient method of inducing differentiation of a pulp cell into an odontoblast. Also provided is an agent for inducing differentiation capable of inducing differentiation into an odontoblast efficiently. The method of inducing differentiation of a pulp cell into an odontoblast includes using a substance capable of activating a Wnt signaling pathway. Further, the agent for inducing differentiation includes a substance capable of activating a Wnt signaling pathway. Specifically, the substance capable of activating a Wnt signaling pathway is any one selected from sodium perchlorate, sodium perchlorate, lithium chloride, Norrin, and R-Spondin2.

5 Claims, 1 Drawing Sheet

(56) References Cited

OTHER PUBLICATIONS

Klein, P.S. et al.: "A molecular mechanism for the effect of lithium on development.", Proc. Natl. Acad. Sci. USA., vol. 93, No. 16, Aug. 6, 1996, pp. 8455-8459.

Orena, S.J. et al.: "Inhibition of glycogen-synthase kinase 3 stimulates glycogen synthase and glucose transport by distinct mechanisms in 3T3-L1 adipocytes.", J. Biol. Chem., vol. 275, No. 21, May 26, 2000, pp. 15765-15772.

Nemoto, E. et al.: "Wnt signaling inhibits cementoblast differentiation and promotes proliferation.", Bone, vol. 44, No. 5, Jan. 14, 2009, pp. 805-812.

Lin, S. et al.: "Norrin attenuates protease-mediated death of transformed retinal ganglion cells.", Mol. Vis., vol. 15, Jan. 12, 2009, pp. 26-37.

Friedman, M.S. et al.: "Wnt11 promotes osteoblast maturation and mineralization through R-spondin 2.", J. Biol. Chem., vol. 284, No. 21, Feb. 12, 2009, pp. 14117-14125.

Chen, J. et al.: "Wnt/beta-catenin signaling plays an essential role in activation of odontogenic mesenchyme during early tooth development.", Dev. Biol., vol. 334, No. 1, Jul. 22, 2009, pp. 174-185.

Scheller, E.L. et al.: "Wnt/beta-catenin inhibits dental pulp stem cell differentiation.", J. Dent. Res., vol. 87, No. 2, Feb. 2008, pp. 126-130.

Peng, L. et al.: "Wnt5a promotes differentiation of human dental papilla cells.", Int. En Dod. J., vol. 43, No. 5, May 2010, pp. 404-412.

Yamashiro, T. et al.: "Wnti0a regulates dentin sialophosphoprotein mRNA expression and possibly links odontoblast differentiation and tooth morphogenesis.", Differentiation, vol. 75, No. 5, Jun. 2007, pp. 452-462.

* cited by examiner fibronectin (FN) (+)

fibronectin (FN) (+)

METHOD FOR INDUCING DIFFERENTIATION OF DENTAL PULP CELLS INTO ODONTOBLASTS

TECHNICAL FIELD

The present invention relates to a field of regenerative medicine of dentin. Specifically, the present invention relates to a method of inducing differentiation of pulp cells into odontoblasts in a site-specific manner. The present invention also relates to an agent for inducing differentiation of pulp cells into odontoblasts. The present invention also relates to a pulp capping material including as an active ingredient the agent for inducing differentiation.

The present application claims priority from Japanese Patent Application No. 2009-262378, which is incorporated herein by reference.

BACKGROUND ART

Hitherto, in a treatment for caries (decayed tooth), there has been employed a treatment method involving removing caries by excavation and filling a resin or cement into a tooth after caries excavation, thereby achieving artificial restoration. When a carious cavity caused by caries is large, pulp excavation is halted once in a state in which part of softened dentin is left, and calcium hydroxide is used as a pulp capping material.

Pulp is a vascular connective tissue that fills a cavity called a pulp cavity present inside a tooth, and is a non-mineralized tissue formed from dental papilla derived from mesoderm. On the other hand, dentin is a hard mineralized tissue present around the pulp cavity. Based on the structural features that pulp is a soft tissue and dentin is a hard tissue, both the tissues have conventionally been regarded as quite different tissues. However, in recent years, there has been a growing trend that pulp and dentin are regarded as embryologically and functionally homologous tissues, and in clinical situations as well, as a dentin-pulp complex.

When a tooth is affected by caries, depending on its degree, there is applied a treatment involving protecting pulp without removing it (direct pulp capping), a treatment involving removing only part of pulp (coronal pulp) and preserving radicular pulp (vital pulpotomy), a treatment involving removing the entire pulp and sealing a cavity with a metal or a resin (pulp extirpation), or the like. However, after pulp removal, there arise problems in that dentin weakens because no nutrient is supplied to a tooth and in that no subjective symptom appears when caries progresses again, resulting in exacerbation of caries, because there is no nerve for transmitting pain. Thus, in recent years, it has been considered that it is preferred to preserve pulp as much as possible in order to keep a tooth in a healthy condition. In order to preserve pulp and keep its function, an indirect pulp capping material or a direct pulp capping material is used depending on a damaged condition of dentin and a pathological condition of pulp. The indirect pulp capping material is used in such a condition that dentin is damaged but pulp is not exposed, and the direct pulp capping material is used in a case where pulp is exposed or a case where pulp is partially amputated by a treatment. As the direct pulp capping material, a calcium hydroxide formulation and a formocresol formulation have conventionally been used. However, calcium hydroxide does not have any action of inducing odontoblasts and hence cannot be expected to promote dentinogenesis. Hitherto, there have been reported, as compounds each having an action of promoting dentinogenesis, a bovine blood extract (Patent Literature 1), polysaccharides such as N-acetyl-glucosamine (Patent Literature 2), a bone morphogenetic protein (BMP), and the like.

Calcium hydroxide stimulates odontoblasts in pulp in about three months to promote production of second dentin in a pulp cavity. As a result, healthy dentin is formed between softened dentin and pulp. After that, the softened dentin is removed. However, in this method, calcium hydroxide does not have any action of promoting proliferation of pulp cells and any action of inducing odontoblasts. Hence, a necrosis layer due to a strong alkali is generated in a pulpal surface brought into contact with calcium hydroxide. Further, this method involves causing degeneration and necrosis of a pulpal tissue and regenerating dentin through the subsequent restoration mechanism, and hence involves problems such as along time required for the method, poor efficiency, and indefinite prognosis.

Dentin is a hard tissue that accounts for a large share of a tooth and is present in a state in which it supports the inner pulp and the surrounding enamel and cementum. Dentin is formed by mineralization of organic substrates synthesized and secreted from odontoblasts. Most of the organic substrates are collagens, and the remainder (about 10%) is non-collagenous proteins (NCPs). It is known that dentin sialophosphoprotein (Dspp, hereinafter, simply referred to as "Dspp"), which is the most common among the NCPs, is synthesized by odontoblasts, and then the protein produces dentin sialoprotein (DSP), dentin glycoprotein (DGP), and dentin phosphoprotein (DPP).

A variety of research has been advanced on a method of inducing differentiation of pulp cells into odontoblasts and a method of regenerating dentin. As an alternative to calcium hydroxide, there is a disclosure of a pulp capping agent (material) for dentinogenesis including a BMP as an active ingredient (Patent Literature 3). Use of a bone inducing factor such as a BMP was attempted to be applied to production of dentin, focusing on the fact that a component of a mineralization substrate forming dentin is very similar to that of bone. However, the factor such as a BMP has an effect of promoting production of a mineralization substrate by already differentiated odontoblasts, but does not promote differentiation of pulp cells into odontoblasts. Hence, the factor has a very limited effect of inducing odontoblasts in an affected tissue.

A method involving regenerating natural dentin and using the natural dentin for a treatment has been proposed and studied. For example, there is a report that a sample obtained by seeding cultured human pulp cells into a hydroxyapatite-tricalcium phosphate complex powder was transplanted subcutaneously into nude mice, extirpation was carried out after 6 weeks, and formation of a hard tissue was confirmed from a hematoxylin/eosin staining image after the extirpation (Non Patent Literature 1). There is also a report that, when RNA extracted from this sample was evaluated using RT-PCR, mRNA of a differentiation marker for odontoblasts was expressed, in other words, the resultant hard tissue was a dentin-like tissue. In this regard, however, an amount of the formed hard tissue is very small, and a larger amount of dentin needs to be regenerated for clinical applications.

As other technologies relating to dentin regeneration, there is a disclosure of a pulp capping agent (material) for dentin regeneration including a collagen-fixed ethylene-vinyl acetate copolymer saponification product (A) and a binder (B) (Patent Literature 4). Such pulp capping agent (material) for dentin regeneration has an excellent function of securing a scaffold for proliferation of cells each having an ability to regenerate dentin. In addition, as a method of regenerating dentin, there is a disclosure of a method of regenerating dentin involving culturing human pulp cells in the presence of 1,25 (dihydroxy) vitamin $D_3$, dexamethasone, and β-glycerophosphate to achieve differentiation into odontoblasts, and culturing and/or transplanting the cells together with a carrier or the like (Patent Literatures 5 and 6). Further, as another method, there is a disclosure of a pulp capping agent (material) for dentinogenesis using polyphosphoric acid (Patent Literature 7). However, any of the literatures merely discloses a technology for regenerating dentin from odontoblasts, and none of the literatures discloses induction of differentiation of pulp cells into odontoblasts.

It is known that tooth development proceeds through a close interaction between an odontogenic epithelium and an odontogenic mesenchymal tissue. Neural crest-derived mesenchymal cells receive a signal from an ectodermal epithelium tissue and are differentiated into pulp cells. Various growth factors are supposed to be involved in this process. As signals involved in tooth development, for example, there are known a BMP, a fibroblast growth factor (FGF), a Wnt, and a sonic hedgehog (Shh). There is also a report suggesting that transforming growth factor (TGF)-β is involved in differentiation of mature pulp cells into odontoblasts.

A basement membrane is present between an epithelium and a mesenchymal tissue, and one of the constituents for the basement membrane is a proteoglycan. Recent research has clarified that a sugar chain of the proteoglycan of the basement membrane plays an important role in Wnt signaling (Non Patent Literature 2). There is a report that the Wnt induces secretion of Dspp in neural crest cells at the development stage (Non Patent Literature 3). That is, Non Patent Literature 3 reports the Wnt at the tooth development stage, but does not report that the Wnt is involved in differentiation of pulp cells into odontoblasts and regeneration in the already formed tooth.

There is a report that, when a mouse p14 lower molar tooth tissue was confirmed by in situ hybridization using a $[_{\alpha\text{-}35}S]$ UTP-labeled RNA probe, Wnt10a was found to be expressed in the basement membrane, and Dspp as an extracellular matrix specific for odontoblasts was found to be expressed in the basement membrane as with Wnt10a (Non Patent Literature 4: see FIG. 1). There is also a report that, when Wnt10a was forcibly expressed in undifferentiated mesenchymal cells C310T1/2 and the cells were cultured with a Matrigel (basement membrane extracts), Dspp mRNA was expressed after 10 days (Non Patent Literature 4: see FIG. 2).

A Wnt signal is conserved across biological species and controls body axis formation and organ formation during early development and cell proliferation and differentiation. It is known that a Wnt signaling pathway includes at least the following three kinds of pathways: 1) a β-catenin pathway, which regulates a transcription factor via intracellular accumulation of β-catenin; 2) a PCP pathway, which controls planar cell polarity via the family of Rho as a low molecular weight G protein; and 3) a $Ca^{2+}$ pathway, which causes intracellular $Ca^{2+}$ recruitment via a trimer G protein to activate protein kinase C (PKC), $Ca^{2+}$/calmodulin-dependent protein kinase II (CaMK II), and the like (Non Patent Literature 5). However, a method of inducing differentiation of pulp cells into odontoblasts to form dentin has not been elucidated yet.

CITATION LIST

Patent Literature

[PTL 1] JP 2002-363084 A
[PTL 2] JP 06-256132 A
[PTL 3] JP 06-340555 A
[PTL 4] JP 2004-292433 A
[PTL 5] JP 2005-341961 A
[PTL 6] JP 2006-211957 A
[PTL 7] JP 2005-263681 A

Non Patent Literature

[NPL 1] Proc. Natl. Acad. Sci. USA, 97(25), 13625-30 (2000)
[NPL 2] J Cell Biol., 162(2), 341-51 (2003)
[NPL 3] Differentiation, 75(5), 52-62 (2007)
[NPL 4] European Cells and Materials, Vol. 14, Suppl. 2, 140 (2007)
[NPL 5] Protein, Nucleic Acid and Enzyme, Vol. 49(10), 1421-1427 (2004)

SUMMARY OF INVENTION

Technical Problem

An object of the present invention is to provide an efficient method of inducing differentiation of a pulp cell into an odontoblast. Another object of the present invention is to provide an agent for inducing differentiation capable of inducing differentiation into an odontoblast efficiently.

Solution to Problem

In order to achieve the above-mentioned objects, the inventors of the present invention have focused on the involvement of a Wnt signal in the differentiation into an odontoblast and have made extensive studies. As a result, the inventors have found for the first time that, when a pulp cell is cultured using a substance capable of activating a Wnt signaling pathway, specifically any one selected from sodium chlorate, sodium perchlorate, lithium chloride, Norrin, and R-Spondin2, Dspp as an extracellular matrix specific for an odontoblast is produced in the cultured pulp cell. Thus, the present invention has been completed.

That is, the present invention includes the following.

1. A method of inducing differentiation of a pulp cell into an odontoblast, including using a substance capable of activating a Wnt signaling pathway.

2. A method of inducing differentiation according to the above-mentioned item 1, in which the substance capable of activating a Wnt signaling pathway includes a substance capable of directly or indirectly activating a Wnt signaling pathway.

3. A method of inducing differentiation according to the above-mentioned item 2, in which the substance capable of indirectly activating a Wnt signaling pathway includes a substance capable of regulating an interaction between a heparan sulfate proteoglycan and a Wnt.

4. A method of inducing differentiation according to the above-mentioned item 3, in which the substance capable of regulating an interaction between a heparan sulfate proteoglycan and a Wnt includes a substance capable of removing a sulfate group from a heparan sulfate proteoglycan.

5. A method of inducing differentiation according to any one of the above-mentioned items 1 to 4, in which the substance capable of activating a Wnt signaling pathway includes any one selected from sodium chlorate, sodium perchlorate, lithium chloride, Norrin, and R-Spondin2.

6. A method of inducing differentiation according to any one of the above-mentioned items 1 to 5, in which the Wnt includes Wnt10a.

7. An agent for inducing differentiation of a pulp cell into an odontoblast, including a substance capable of activating a Wnt signaling pathway.

8. An agent for inducing differentiation according to the above-mentioned item 7, in which the substance capable of activating a Wnt signaling pathway includes any one selected from sodium chlorate, sodium perchlorate, lithium chloride, Norrin, and R-Spondin2.

9. A pulp capping material, including as an active ingredient the agent for inducing differentiation according to the above-mentioned item 7 or 8.

10. A pulp capping material according to the above-mentioned item 9, further including fibronectin.

Advantageous Effects of Invention

The use of the substance capable of activating a Wnt signaling pathway, specifically any one selected from sodium chlorate, sodium perchlorate, lithium chloride, Norrin, and R-Spondin2 significantly enhances the expression of Dspp as an extracellular matrix specific for an odontoblast in a pulp-derived cell line. As a result, the substance capable of activating a Wnt signaling pathway, specifically any one selected from sodium chlorate, sodium perchlorate, lithium chloride, Norrin, and R-Spondin2, is capable of serving as the agent for inducing differentiation of a pulp cell into an odontoblast. In addition, the pulp capping material including as an active ingredient the agent for inducing differentiation of the present invention has actions of inducing differentiation of a pulp cell into an odontoblast and promoting the subsequent dentinogenesis as well as an action of protecting an exposed pulpal surface.

DESCRIPTION OF EMBODIMENTS

Figure 1:
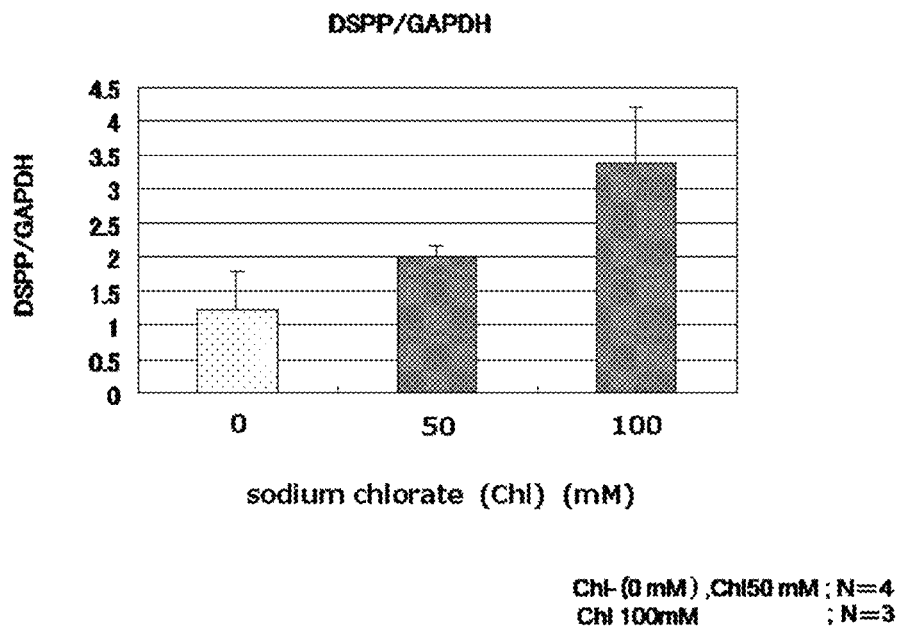
FIG. 1 A graph showing the expression of Dspp when sodium chlorate is added at different concentrations to MEDP cells as a pulp-derived cell line and the cells are cultured (Example 1).

The present invention relates to a method of inducing differentiation of a pulp cell into an odontoblast, including using a substance capable of activating a Wnt signaling pathway.

The inventors of the present invention have confirmed that the induction of Dspp occurs only when Wnt10a-expressing cells are cultured on a Matrigel made from basement membrane extracts, and have found that regulation by both of a Wnt signal and a certain component included in the basement membrane is essential for the differentiation into odontoblasts. Based on this finding, the inventors of the present invention have observed tooth phenotypes of Sulf1/Sulf2 (endosulfatases) double knockout mice. As a result, the inventors have confirmed that dentinogenesis is significantly suppressed in the double knockout mice as compared to wild-type ones.

Based on the above-mentioned findings, the inventors of the present invention have confirmed for the first time an action of inducing differentiation into odontoblasts by allowing the substance capable of activating a Wnt signaling pathway to act on a pulp-derived cell line. As a result, the inventors have found that Dspp, which is the most common as a non-collagenous protein among organic substrates synthesized and secreted from odontoblasts, is produced in the pulp derived cell line on which the substance capable of activating a Wnt signaling pathway has been allowed to act.

In the present invention, the substance capable of activating a Wnt signaling pathway may be a substance capable of directly activating a Wnt signaling pathway or may be a substance capable of indirectly activating a Wnt signaling pathway. Examples of the substance capable of directly activating a Wnt signaling pathway include any one selected from lithium chloride, Norrin, and R-Spondin2, and examples of the substance capable of indirectly activating a Wnt signaling pathway include sodium chlorate, sodium perchlorate, and endosulfatases.

Herein, the substance capable of directly activating a Wnt signaling pathway refers to a substance that directly acts on a substance acting in a canonical Wnt signaling pathway to activate the Wnt signaling pathway. The canonical Wnt signaling pathway, specifically a Wnt/β-catenin pathway, regulates cell fate determination in the development of vertebrates and invertebrates. A Wnt ligand is a secreted glycoprotein that binds to Frizzled receptors, which triggers a signal cascade, resulting in the dissociation of a multifunctional kinase GSK-3β from an APC/Axin/GSK-3β complex. In this context, it is known that GSK-3 has a suppressive role in the Wnt signaling pathway (Cell Research, (1):28-32 (2005)). It is said that lithium chloride has an action of suppressing GSK-3 (J Biol Chem., 275 (21):15765-72 (2000)). From the above-mentioned viewpoints, specific examples of the substance capable of directly activating a Wnt signaling pathway include lithium chloride. GSK-3 has a suppressive role in the Wnt signaling pathway. Hence, the addition of lithium chloride is capable of activating the Wnt signaling pathway. It is said that any of Norrin and R-Spondin2 is a protein capable of directly activating a Wnt signaling pathway.

Herein, examples of the substance capable of indirectly activating a Wnt signaling pathway include a substance capable of regulating an interaction between a heparan sulfate proteoglycan and a Wnt. Recent research has clarified that a sugar chain of a proteoglycan in the basement membrane plays an important role in Wnt signaling. The Wnt is bound to a sugar chain of the heparan sulfate proteoglycan very strongly. However, when a sulfate group is removed from heparan sulfate by an endosulfatase, the affinity of the sugar chain to the Wnt lowers, and the Wnt, which has been bound to the heparan sulfate proteoglycan, is dissociated therefrom and transferred to a Wnt receptor, resulting in the activation of a Wnt signal. In the present invention, examples of the substance capable of regulating an interaction between a heparan sulfate proteoglycan and a Wnt include a substance capable of reducing the affinity of a heparan sulfate proteoglycans to a Wnt. Examples of such substance include a substance capable of removing a sulfate group from a heparan sulfate proteoglycan. Specific examples thereof include sodium chlorate, sodium perchlorate, and endosulfatases. Of those, sodium chlorate and sodium perchlorate are preferred. Sodium chlorate has an action capable of removing a sulfate group from a heparan sulfate proteoglycan (J Biol Chem., 263(26):12886-92 (1988)). The removal of a sulfate group from a heparan sulfate proteoglycan reduces the affinity of a sugar chain to a Wnt. As a result, the Wnt, which has been bound to the heparan sulfate proteoglycan, is dissociated therefrom and transferred to a Wnt receptor, and thus a Wnt signaling pathway is activated.

The Wnt is one of the intercellular signal molecules. It is known that the Wnt family includes 17 or more members at present. Wnt10a is found to be expressed in the basement membrane. Among Wnt molecules other than Wnt10a, Wnt5a and Wnt10b are found to be expressed in ameloblasts and cementoblasts. In the present invention, the kind of the Wnt to be activated in the Wnt signaling pathway is not particularly limited. However, it is particularly suitable to activate a pathway including Wnt10a in order to induce the differentiation of pulp cells into odontoblasts.

A tooth is formed from a tooth germ, grows through processes of the bud stage, the cap stage, and the bell stage, and erupts in the mouth. The tooth germ is the primordium of the tooth and periodontal tissues and is derived from an ectodermal mesenchymal tissue. Further, the tooth germ is divided into three tissues, i.e., enamel organ, dental papilla, and dental follicle. The tooth is structured of three major hard tissues, i.e., enamel, dentin, and cementum. Pulp is present in the interior of these hard tissues (pulp cavity) and dentin is present outside the pulp. The pulp is of the same origin as dental follicular cells. In this context, the dental follicular cells are mesenchymal tissues derived from dental papilla observed at the development stage. It is said that the dental follicular cells are differentiated into periodontal tissue cells such as periodontium, cementum, and alveolar bone. Odontoblasts are present in the outermost layer of the pulp, and the differentiation into odontoblasts occurs only in the boundary between the epithelium and the mesenchymal tissue.

In the epithelium of all tissues and organs, there is a unique extracellular matrix (ECM) called the basement membrane lining the epithelium. The basement membrane is present between an epithelial cell layer such as enamel and an interstitial cell layer (pulp cell layer) or the like. As constituent substances for the basement membrane, for example, there are given type IV collagen, laminin, and a heparan sulfate proteoglycan. The heparan sulfate proteoglycan is present in a state in which a heparan sulfate is added to a protein to serve as a core called a core protein, such as a proteoglycan such as perlecan, syndecan, glypican, or agrin. The heparan sulfate has a repetitive structure of disaccharide units of N-acetylglucosamine and glucuronic acid or iduronic acid and exhibits diversity depending on the number of sulfate groups on a sugar chain. In the present invention, the heparan sulfate proteoglycan is a collective term for glucosaminoglucans each having added thereto such heparan sulfate and is not particularly limited.

The present invention also encompasses an agent for inducing differentiation of pulp cells into odontoblasts, including a substance capable of activating a Wnt signaling pathway. As described above, specific examples of the substance capable of activating a Wnt signaling pathway include sodium chlorate, sodium perchlorate, lithium chloride, endosulfatases, Norrin, and R-Spondin2. Of those, sodium chlorate, sodium perchlorate, or lithium chloride is preferred.

The present invention also encompasses a pulp capping material including as an active ingredient the above-mentioned agent for inducing differentiation. The pulp capping material of the present invention has actions of inducing differentiation of pulp cells into odontoblasts and promoting dentinogenesis as well as an action of protecting an exposed pulpal surface. The pulp capping material of the present invention may be used by being applied onto or filled into the amputated pulpal surface of a cavity after a general treatment for caries such as opening of pulp chamber or extirpation of pulp. The pulp capping material of the present invention may be used in combination with a direct pulp capping material or an indirect pulp capping material. The pulp capping material of the present invention may be applied before or after the application of the direct pulp capping material or the indirect pulp capping material, or may be applied by being mixed with the direct pulp capping material or the indirect pulp capping material. Herein, the "direct pulp capping material" refers to a medicament for protecting a pulpal tissue when pulp is partially exposed, and for example, a calcium hydroxide formulation is used. The "indirect pulp capping material" refers to a medicament used for the purposes of blocking of external stimulation, sterilization, and the like when dentin is thin but pulp is not exposed, and for example, a zinc oxide eugenol formulation or a zinc oxide creosote formulation is used.

The content of the agent for inducing differentiation such as sodium chlorate, sodium perchlorate, or lithium chloride in the pulp capping material of the present invention is not particularly limited. In the case of sodium chlorate or sodium perchlorate, for example, the content is suitably 5 to 500 mM, preferably 50 to 100 mM. Further, in the case of lithium chloride, for example, the content is suitably 2 to 200 mM, preferably 5 to 50 mM, more preferably about 50 mM.

The agent for inducing differentiation such as sodium chlorate, sodium perchlorate, or lithium chloride in the pulp capping material of the present invention may be used as it is or used as a mixture with a pharmacologically and pharmaceutically acceptable additive to prepare various formulations in forms suitable for being applied to an affected area. Examples of the formulation forms suitable for the pulp capping material of the present invention include injections, liquids for external use (infusions, liniments), solid preparations (granules, fine subtilaes, powdered medicines, ointments, tablets), and ointments. The agent for inducing differentiation of the present invention may include fibronectin (FN), for example.

As the pharmacologically and pharmaceutically acceptable additive, there may be used, for example, an excipient, a disintegrator or a disintegrating aid, a binder, a lubricant, a coating, a coloring, a diluent, a base, a solvent or a dissolving aid, a tonicity agent, a pH adjuster, a stabilizer, an antiseptic, a preservative, a dispersant, an emulsifier, a gelling agent, a thickener, a tackifier, and a corrigent.

The gelling agent may be, for example, one that absorbs a tooth exudate to gelate. Alternatively, a form formed of a powder and a liquid may be mixed and kneaded before use. The pulp capping material of the present invention may further include other active ingredients such as a microbicide, an antibiotic, and an anti-inflammatory agent.

The pulp capping material of the present invention may be carried by a carrier in order to facilitate the application of an active ingredient of a medicament to an affected area and to allow an active ingredient to be kept in an affected area for a period of time enough to induce differentiation into odontoblasts. Thus, the pulp capping material of the present invention may be in a form of a dental material in which the agent for inducing differentiation of the present invention such as sodium chlorate, sodium perchlorate, or lithium chloride and an appropriate aid are fixed or impregnated into a structure having a shape such as a monofilament, a film, fiber assembly, a sponge, or a fine particle.

The dose of the pulp capping material of the present invention is not particularly limited and is appropriately adjusted depending on, for example, the symptom (degree of progression of decayed tooth) and age of a patient and a dosage form.

EXAMPLES

Hereinafter, the present invention is more specifically described by way of examples. However, the present invention is by no means limited to the scope of the following examples.

Example 1

Induction of Differentiation into Odontoblasts Using Sodium Chlorate (NaClO$_3$)

In this example, MEDP cells as a pulp-derived cell line were cultured in a system including NaClO$_3$, and the expression of Dspp in the cultured cells was confirmed. The expression of Dspp was confirmed by PCR.

The MEDP cells were cultured using a DMEM medium containing 10% v/v fetal bovine serum (FBS). The cells were suspended in the medium so that the number of the cells was 3.7×10$^5$ cells/ml, and 5 ml of the cell suspension were added to a culture vessel having a diameter of 6 cm and cultured. The culture was carried out using a culture vessel coated with fibronectin (FN) at 37±0.5° C. On day 1 of the culture, NaClO$_4$ was added so that the final concentration was 50 mM or 100 mM, and the cells were cultured for an additional 7 days.

After mRNA had been extracted from the cultured cells using an RNeasy Mini Kit™ (manufactured by QIAGEN), reverse transcription was carried out using a PrimeScript™ Reverse Transcriptase (manufactured by TAKARA) to prepare cDNA, which was used as a sample for PCR. The extraction of mRNA and the preparation of cDNA were carried out in accordance with the manufacturer's instructions. Primers formed of base sequences set forth in SEQ ID NOS: 1 and 2 of the sequence listing were used as primers for amplification of DSPP, and primers formed of base sequences set forth in SEQ ID NOS: 3 and 4 of the sequence listing were used as primers for amplification of GADPH as a control gene. The PCR was carried out using a LightCycler™ (manufactured by Roche). The expression amount of DSPP was confirmed with a relative ratio between an amplification product of DSPP and an amplification product of GADPH.

A. Primers for amplification of DSPP

```
forward    5'-AGCCGTGGAGATGCTTCTTA-3'    (SEQ NO: 1)
reverse    5'-TCACTCTGGCTGTCACCATC-3'    (SEQ NO: 2)
```

B. Primers for amplification of GADPH

```
forward    5'-TGCACCACCAACTGCTTAG-3'     (SEQ NO: 3)
reverse    5'-GGATGCAGGGATGATGTTC-3'     (SEQ NO: 4)
```

The results confirmed that, in the culture in the system including NaClO$_3$, the expression of Dspp was significantly enhanced and the differentiation of undifferentiated pulp cells into odontoblasts was induced. The administration of NaClO$_3$ inhibits the sulfation of a heparan sulfate proteoglycan and dissociates a Wnt from the cell membrane or the basement membrane, which can bind to a Wnt receptor. Thus, the administration of NaClO$_3$ is capable of indirectly activating a Wnt signaling pathway. It was estimated that the differentiation of undifferentiated pulp cells into odontoblasts was promoted as a result of the foregoing fact (FIG. 1).

Example 2

Induction of Differentiation into Odontoblasts Using Lithium Chloride (LiCl)

In this example, MEDP cells as a pulp-derived cell line were cultured in a system including LiCl, and the expression of Dspp in the cultured cells was confirmed. The expression of Dspp was confirmed by PCR.

A treatment for inducing differentiation was carried out by the same technique as that of Example 1 except that LiCl was used in place of NaClO$_3$ and LiCl was added so that the final concentration was 5 mM or 50 mM on day 1 of the culture. Then, the expression of Dspp was confirmed.

Figure 2:
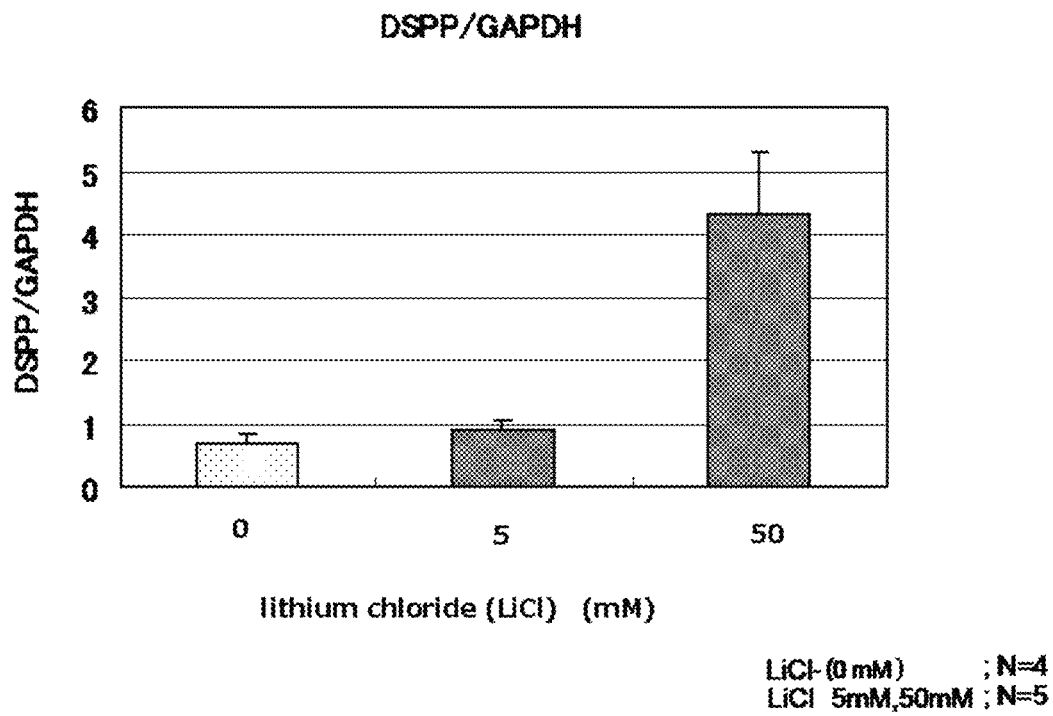
FIG. 2 A graph showing the expression of Dspp when lithium chloride is added at different concentrations to MEDP cells as a pulp-derived cell line and the cells are cultured (Example 2).

The results confirmed that, in the culture of the pulp cells in the system including LiCl, the expression of Dspp was significantly enhanced and the differentiation of undifferentiated pulp cells into odontoblasts was induced. It is said that LiCl has an action of suppressing GSK-3. GSK-3 has a suppressive role in the Wnt signaling pathway, and LiCl is capable of directly activating the Wnt signaling pathway by suppressing GSK-3. It was estimated that the differentiation of undifferentiated pulp cells into odontoblasts was promoted as a result of the foregoing fact (FIG. 2).

Example 3

Induction of Differentiation into Odontoblasts Using Sodium Perchlorate (NaClO$_4$)

In this example, MEDP cells as a pulp-derived cell line were cultured in a system including NaClO$_4$, and the expression of Dspp in the cultured cells was confirmed. The expression of Dspp was confirmed by PCR.

A treatment for inducing differentiation was carried out by the same technique as that of Example 1 except that NaClO$_4$ was used in place of NaClO$_3$. Then, the expression of Dspp was confirmed.

Example 4

Induction of Differentiation into Odontoblasts Using Norrin

In this example, MEDP cells as a pulp-derived cell line are cultured in a system including Norrin, and the expression of Dspp in the cultured cells is confirmed. The expression of Dspp is confirmed by PCR.

A treatment for inducing differentiation is carried out by the same technique as that of Example 1 except that Norrin (R&D Systems, Inc.: catalog No.: 3014-NR) is used in place of NaClO$_3$. Then, the expression of Dspp is confirmed. The addition concentration of Norrin is to be considered.

Example 5

Induction of Differentiation into Odontoblasts Using R-Spondin2

In this example, MEDP cells as a pulp-derived cell line are cultured in a system including R-Spondin2, and the expression of Dspp in the cultured cells is confirmed. The expression of Dspp is confirmed by PCR.

A treatment for inducing differentiation is carried out by the same technique as that of Example 1 except that R-Spondin2 (R&D Systems, Inc.: catalog No.: 3266-RS/CF) is used in place of NaClO₃. Then, the expression of Dspp is confirmed. The addition concentration of R-Spondin2 is to be considered.

INDUSTRIAL APPLICABILITY

As described in detail above, it was found that the use of the substance capable of activating a Wnt signaling pathway of the present invention, specifically sodium chlorate, sodium perchlorate, or lithium chloride, significantly enhanced the expression of Dspp as an extracellular matrix specific for odontoblasts in the pulp-derived cell line. As a result, the substance capable of activating a Wnt signaling pathway is capable of serving as an agent for inducing differentiation of pulp cells into odontoblasts. In addition, the pulp capping material including as an active ingredient the agent for inducing differentiation of the present invention has actions of inducing differentiation of pulp cells into odontoblasts and promoting dentinogenesis as well as an action of protecting an exposed pulpal surface.

The agent for inducing differentiation of pulp cells into odontoblasts of the present invention has an effect of promoting the induction of differentiation of pulp cells into odontoblasts through its direct action on pulp. Thus, in its clinical applications, it is expected that dentin is actively regenerated just below caries by directly applying the agent for inducing differentiation to a caries-affected area or filling a paste including the agent for inducing differentiation into a caries-affected area. After the confirmation of sufficient secondary (reparative) dentin formation, a carious lesion is removed, and a reparative treatment with a resin or a metal is carried out.

The invention claimed is:

1. A method of inducing differentiation of a pulp (MEDP) cell into an odontoblast comprising administering to said cell an effective amount of a substance under conditions sufficient to cause differentiation of said cell into an odontoblast, wherein said substance is selected from the group consisting of sodium chlorate, sodium perchlorate, Norrin, R-Spondin2, or a combination thereof.

2. The method of inducing differentiation according to claim 1, wherein the substance comprises Norrin.

3. The method of inducing differentiation according to claim 1, wherein the substance comprises R-Spondin2.

4. The method of inducing differentiation according to claim 1, wherein the substance comprises sodium chlorate.

5. The method of inducing differentiation according to claim 1, wherein the substance comprises sodium perchlorate.

* * * * *

```
                        SEQUENCE LISTING

<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: Synthesized forward primer for amplifying mice
      dspp genes

<400> SEQUENCE: 1
agccgtggag atgcttctta                                                   20

<210> SEQ ID NO 2
<211> LENGTH: 20
<212> TYPE: DNA
<213> ORGANISM: Artificial
<220> FEATURE:
<223> OTHER INFORMATION: Synthesized reverse primer for amplifying mice
      dspp genes

<400> SEQUENCE: 2
tcactctggc tgtcaccatc                                                   20

<210> SEQ ID NO 3
<211> LENGTH: 19
<212> TYPE: DNA
<213> ORGANISM: Artificial
<220> FEATURE:
<223> OTHER INFORMATION: Synthesized forward primer for amplifying mice
      gapdh genes

<400> SEQUENCE: 3
tgcaccacca actgcttag                                                    19

<210> SEQ ID NO 4
<211> LENGTH: 19
<212> TYPE: DNA
<213> ORGANISM: Artificial
<220> FEATURE:
<223> OTHER INFORMATION: Synthesized reverse primer for amplifying mice
      gapdh genes

<400> SEQUENCE: 4
ggatgcaggg atgatgttc                                                    19
```